United States Patent

Greindl et al.

[11] Patent Number: 5,994,582
[45] Date of Patent: Nov. 30, 1999

[54] PREPARATION OF SUBSTITUTED GUANIDINE DERIVATIVE

[75] Inventors: Thomas Greindl, Bad Dürkheim; Günter Scherr, Ludwigshafen; Rolf Schneider, Mannheim; Klaus Mundinger, Limburgerhof, all of Germany

[73] Assignee: BASF Aktiengesellschaft, Germany

[21] Appl. No.: 09/179,464

[22] Filed: Oct. 27, 1998

[30] Foreign Application Priority Data

Nov. 4, 1997 [DE] Germany .......................... 197 48 695

[51] Int. Cl.⁶ .................................................. C07C 249/02
[52] U.S. Cl. ............................................. 562/560; 564/241
[58] Field of Search .............................. 562/560; 564/241

[56] References Cited

U.S. PATENT DOCUMENTS

| | | | |
|---|---|---|---|
| 2,727,922 | 12/1955 | Lecher et al. ............................ | 260/564 |
| 4,421,602 | 12/1983 | Brunnmueller et al. ................. | 162/168 |
| 4,444,667 | 4/1984 | Burkert et al. .......................... | 210/735 |
| 4,774,285 | 9/1988 | Pfohl et al. .............................. | 525/60 |
| 4,880,497 | 11/1989 | Pfohl et al. .............................. | 162/135 |
| 5,719,319 | 2/1998 | Weiss et al. ............................. | 562/560 |

FOREIGN PATENT DOCUMENTS 78077364  6/1978  Japan .

OTHER PUBLICATIONS

*J. Am. Chem. Soc.*, 114 (1992) pp. 9386–9390.
CA 128: 230086 Reaction of N–pentafluorophenylcarbon-imidoyl chloride with aromatic amines. Petrova et al., 1998.

*Primary Examiner*—Joseph K. McKane
*Attorney, Agent, or Firm*—Keil & Weinkauf

[57] ABSTRACT

Substituted guanidine derivatives of the formula I,

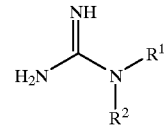

are prepared by reacting haloformamidinium salts of the formula II,

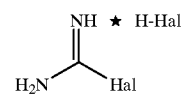

where Hal can be Cl, F, Br and I, with primary or secondary amines of the formula III

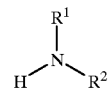

where the substituents $R^1$ and $R^2$ have the meanings explained in the description.

5 Claims, No Drawings

PREPARATION OF SUBSTITUTED GUANIDINE DERIVATIVE

The invention relates to a process for preparing substituted guanidine derivatives by reacting haloformamidinium salts with primary or secondary amines.

Substituted guanidinium compounds are widespread in nature. Important representatives of this class of substances are, for example, amino acids such as arginine and creatine. In addition, substituted guanidine derivatives are known as sterically hindered bases, as biocides and as complex ligands. However, the industrial applicability of most of the compounds of this type is greatly restricted owing to the high costs of their preparation.

One example of a biologically active guanidine derivative is creatine which, as "the cell's energy carrier" is employed as dietary supplement in the food and drugs sectors.

The preparation of creatine is described, for example, in EP-A-0 754 679 and the further literature quoted therein, the maximum yields obtained being only 70%. One disadvantage of this synthesis of guanidinium compounds is that aqueous solutions of pure cyanamide are employed in all cases. However, this solution is very costly and, owing to the instability of cyanamide, generally not widely available.

Alternative syntheses of guanidinium salts make use of O-alkylisoureas or O-alkylisothioureas. Thus, in JP 077364 a solution of sodium sarcosinate is reacted with O-methylisourea methyl sulfate to give creatine in yields of 80%. It is necessary in all these syntheses to use alkylating agents such as dimethyl sulfate, and the selectivity is frequently inadequate owing to the occurrence of multiple alkylations.

It is an object of the present invention to provide a process for preparing substituted guanidinium compounds which does not have the abovementioned disadvantages.

We have found that this object is achieved by a process for preparing substituted guanidine derivatives of the formula I,

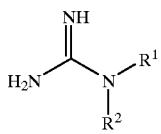
I which comprises reacting haloformamidinium salts of the formula II,

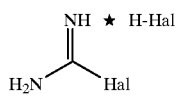
II where Hal can be Cl, F, Br and I, with primary or secondary amines of the formula III

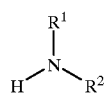
III where the substituents $R^1$ and $R^2$ have the following meanings independently of one another:

$R^1$ H, $C_1$–$C_{20}$-alkyl, $C_2$–$C_{10}$-alkenyl, $C_3$–$C_8$-cycloalkyl;

$R^2$ $C_1$–$C_{20}$-alkyl, $C_2$–$C_{10}$-alkenyl, $C_3$–$C_8$-cycloalkyl, —($C_1$–$C_{20}$-alkylene)—COOR$^3$, —$C_1$–$C_{20}$-alkylene)—CONR$^4$R$^5$, —($C_1$–$C_{20}$-alkylene)—CN, —($C_1$–$C_{20}$-alkylkene)—SO$_2$R$^6$, —[(CH$_2$)$_m$—X—]$_p$—[(CH$_2$)$_n$—Y—]$_q$—[(CH$_2$)$_o$]$_r$—Z;

m, n, o
0 to 10;

p, q, r
0 to 50,000;

X O, NH;

Y N—[(CH$_2$)$_m$—X—]$_p$—[(CH$_2$)$_n$—Y—]$_q$—[(CH$_2$)$_o$]$_r$—Z;

Z OH, NH$_2$;

$R^3$ H, $C_1$–$C_{20}$-alkyl, $C_2$–$C_{10}$-alkenyl, $C_3$–$C_8$-cycloalkyl, $C_6$–$C_{18}$-aryl, Na, K, Li, Ca, Mg, N(R$^7$)$_4$;

$R^4$ and $R^5$ independently of one another H, $C_1$–$C_{20}$-alkyl, $C_2$–$C_{10}$-alkenyl, $C_3$–$C_8$-cycloalkyl, $C_6$–$C_{18}$-aryl;

$R^6$ OR$^8$, N(R$^9$)$_2$;

$R^7$ H, $C_1$–$C_{20}$-alkyl;

$R^8$ H, $C_1$–$C_{20}$-alkyl, $C_2$–$C_{10}$-alkenyl, $C_3$–$C_8$-cycloalkyl, $C_6$–$C_{18}$-aryl, Na, K, Li, Ca, Mg, N(R$^7$)$_4$;

$R^9$ H, $C_1$–$C_{20}$-alkyl, $C_2$–$C_{10}$-alkenyl, $C_3$–$C_8$-cycloalkyl, $C_6$–$C_{18}$-aryl.

The novel process satisfies in particular limiting commercial conditions such as low costs of starting materials, simplicity of industrial implementation, improved yields and adequate purity of the product.

Suitable in principle for reaction with haloformamidinium salts of the formula II are all the claimed amines of the formula III. These may be both aliphatic or cycloaliphatic primary or secondary amines, and amino carboxylic acids and amino sulfonic acids and derivatives thereof. It is also possible in the novel process to react primary and secondary amines which comprise additional amino or imino groups, such as amino-containing oligomers and polymers.

Alkyl radicals which may be mentioned for $R^1$ to $R^5$ and for $R^7$ to $R^9$ are branched or unbranched $C_1$–$C_{20}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Alkenyl radicals which may be mentioned for $R^1$ to $R^5$ and for $R^8$ and $R^9$ are branched or unbranched $C_2$–$C_{10}$-alkenyl chains, preferably vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

Alkylene radicals which may be mentioned for $R^2$ are branched or unbranched $C_1$–$C_{20}$-alkylene chains, preferably methylene, ethylene, n-propylene, 1-methylethylene, n-butylene, 1-methylpropylene, 2-methylpropylene, 1,1-dimethylethylene, n-pentylene, 1-methylbutylene, 2-methylbutylene, 3-methylbutylene, 2,2-dimethylpropylene, 1-ethylpropylene, n-hexylene, 1,1-dimethylpropylene, 1,2-dimethylpropylene, 1-methylpentylene, 2-methylpentylene, 3-methylpentylene, 4-methylpentylene, 1,1-dimethylbutylene, 1,2-dimethylbutylene, 1,3-dimethylbutylene, 2,2-dimethylbutylene, 2,3-dimethylbutylene, 3,3-dimethylbutylene, 1-ethylbutylene, 2-ethylbutylene, 1,1,2-trimethylpropylene, 1,2,2-trimethylpropylene, 1-ethyl-1-methylpropylene, 1-ethyl-2-methylpropylene, n-heptylene, n-octylene, n-nonylene, n-decylene, n-undecylene, n-dodecylene, n-tridecylene, n-tetradecylene, n-pentadecylene, n-hexadecylene, n-heptadecylene, n-octadecylene, n-nonadecylene or n-eicosylene.

The 1- to 20-membered alkylene chains may be substituted by the following radicals:

$C_1$–$C_6$-alkyl, for example methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl;

mercaptomethyl, 1-aminobutyl, 1-carboxyethyl;

arylalkyl, for example benzyl, p-hydroxybenzyl, indolylmethyl.

Cycloalkyl radicals which may be mentioned for $R^1$ to $R^5$ and for $R^8$ and $R^9$ are branched or unbranched $C_3$–$C_8$-cycloalkyl radicals, preferably cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethyl-cyclopropyl or cyclooctyl.

The cycloalkyl radicals may be substituted by one or more, e.g. 1 to 3, radicals such as halogen, e.g. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals, or comprise 1 to 3 heteroatoms such as sulfur, nitrogen, whose free valences can be saturated by hydrogen or $C_1$–$C_4$-alkyl, or oxygen in the ring.

Suitable and preferred alkoxy radicals for $R^6$ are those having 1 to 20 carbon atoms, preferably having 1 to 12 carbon atoms, particularly preferably having 1 to 8 carbon atoms.

Examples which may be mentioned are:

| | |
|---|---|
| methoxy- | ethoxy- |
| isopropoxy- | n-propoxy- |
| 1-methylpropoxy- | n-butoxy- |
| n-pentoxy- | 2-methylpropoxy- |
| 3-methylbutoxy- | 1,1-dimethylpropoxy- |
| 2,2-dimethylpropoxy- | hexoxy- |
| 1-methyl-1-ethylpropoxy- | heptoxy- |
| octoxy- | 2-ethylhexoxy- |

Suitable and preferred mono- or disubstituted amino radicals for $R^6$ are those comprising alkyl radicals having 1 to 20, preferably 1 to 12, carbon atoms, such as methyl, n-propyl, n-butyl, 2-methylpropyl, 1,1-dimethylpropyl, hexyl, heptyl, 2-ethylhexyl, isopropyl, 1-methylpropyl, n-pentyl, 3-methylbutyl, 2,2-dimethylpropyl, 1-methyl-1-ethylpropyl and octyl.

Suitable tetraalkylammonium radicals for $R^3$ and $R^8$ are those comprising alkyl radicals having 1 to 20, preferably 1 to 12, particularly preferably 1 to 6, carbon atoms, such as methyl, n-propyl, isopropyl, 2-methylpropyl, 1,1-dimethylpropyl, 1-methylpropyl, 2,2-dimethylpropyl, 1-methyl-1-ethylpropyl, n-butyl, 3-methylbutyl, n-pentyl and hexyl.

Aryl means aromatic rings or ring systems having 6 to 18 carbon atoms in the ring system, for example phenyl or naphthyl, each of which may be substituted by one or more radicals such as halogen, e.g. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals. Unsubstituted or substituted phenyl, methoxyphenyl and naphthyl are preferred.

Amines which are preferably used are all primary and secondary amines which are soluble in water or in water-miscible solvents. Preferred representatives among the simple amines are, inter alia, methylamine, ethylamine, n-propylamine, 2-propylamine, butylamine, isobutylamine, aniline, benzylamine and anthranilic acid. Further amino-containing compounds which are preferably employed are, inter alia, taurine and amino carboxylic acids such as glycine, alanine, valine, proline, leucine, phenylalanine, lysine, methionine, cysteine, aspartic acid, iminodiacetic acid, sarcosine and their esters, amides and nitriles and their salts.

Sarcosine is the very particularly preferred compound of the formula III, which can be used both as free acid and, in particular, as Na or K salt in the form of a 5 to 60% by weight, preferably 35 to 45% by weight, aqueous solution.

It is also possible to employ water-soluble, amino-containing oligomers and polymers in the novel process, such as alkylenediamines, dialkylenetriamines and so on up to polyalkylenepolyamines or polyetherdiamines. Preferred representatives of this group are ethylenediamine, propylenediamine, butylenediamine, hexamethylenediamine, diethylenetriamine, triethylenetetramine, tetraethylenepentamine, pentaethylenehexamine, hexaethyleneheptamine and branched or linear polyalkylenepolyamines.

Suitable and preferred polyalkylenepolyamines are polyethyleneimines which have, for example, molecular weights of from 200 to 10 million, preferably 1000 to 3 million. Polyethyleneimines with molecular weights of from 2000 to 1,300,000 are particularly preferably employed.

The polyetherdiamines are prepared, for example, by reacting polyalkylene glycols with ammonia. The polyalkylene glycols may contain 2 to 50, preferably 2 to 40 alkylene oxide units. Possible examples thereof are polyethylene glycols, polypropylene glycols, polybutylene glycols or else block copolymers of ethylene glycol and propylene glycol, block copolymers of ethylene glycol and butylene glycol or block copolymers of ethylene glycol, propylene glycol and butylene glycol. Suitable for preparing the polyether diamines apart from the block copolymers are random copolymers of ethylene oxide and propylene oxide, with or without butylene oxide. Polyetherdiamines are additionally derived from polytetrahydrofurans having 2 to 75 tetrahydrofuran units. The polytetrahydrofurans are likewise converted by reaction with ammonia into the corresponding α,ω-polyetherdiamines. Polyethylene glycols or block copolymers of ethylene glycol and propylene glycol are preferably used for preparing the polyetherdiamines.

Further suitable amino-containing water-soluble polymers are polyvinylamines, which are obtainable by homo- and/or copolymerization of N-vinylformamide and subsequent hydrolysis of the polymers, and polymers containing vinylamine units. Substances of this type are know, cf. EP-B-0 071 050 and EP-B-0 216 387. Suitable polymers which are preferred are hydrolyzed homopolymers of N-vinylformamide having a degree of hydrolysis of from 1 to 100, preferably 80 to 100, % and partially or completely hydrolyzed copolymers of N-vinylformamide and vinyl formate or vinyl acetate. The N-vinylformamide units in the copolymers are preferably 80 to 100% hydrolyzed. Depending on the hydrolysis conditions, the monomers such as the vinyl formate or vinyl acetate units in the polymer can be partially or completely hydrolyzed to vinyl alcohol units. Further comonomers suitable for preparing hydrolyzed copolymers of N-vinylformamide are monoethylenically unsaturated carboxylic acids such as acrylic acid, methacrylic acid or maleic acid, N-vinylpyrrolidone and acrylonitrile.

Further amino-containing water-soluble polymers are polyallylamines. These polymers contain at least 3 allylamine units and have molecular weights of up to 10 million.

The haloformamidinium salts used to synthesize substituted guanidinium compounds are stable compounds in pure form. This is particularly true of chloroformamidine hydrochloride, which is preferably used and can be obtained both as described in J. Am. Chem. Soc. 114 (1992) 9386–9390 from pure cyanamide by reaction with hydrogen chloride, and by reacting calcium cyanamide (nitrolime), which is very cheap, with hydrochloric acid as described in U.S. Pat. No. 2,727,922.

According to U.S. Pat. No. 2,727,922, chloroformamidinium chloride can be prepared by using nitrolime, which is very cheap and widely available, in place of costly cyanamide. Nitrolime means products which result, for example, on reaction of $CaC_2$ with $N_2$ at from 800 to 1100° C. As a rule, they contain from 5 to 98% by weight, preferably 20 to 95% by weight, particularly preferably 30 to 90% by weight, of calcium cyanamide. The industrially obtainable gray to black nitrolime contains in addition to calcium cyanamide, depending on the degree of purity, also impurities such as carbon, calcium carbide, CaO and traces of metals, normally in amounts <1%. It is, of course, also possible to use pure calcium cyanamide, but it is particularly advantageous, because considerably more economical, to employ technical nitrolime. The latter is preferably employed with a particle size distribution of from 1 to 100 $\mu$m, preferably 20 to 80 $\mu$m. However, it is also possible to use granulated, extruded or otherwise compacted material.

A particular advantage of the process is that the chloroformamidinium chloride which is produced from hydrochloric acid and nitrolime in an aqueous synthesis can be further reacted directly, after removal of the carbon which is formed and of the insoluble inorganic salts, without further purification to give the corresponding guanidinium compound.

If hydrobromic acid or hydroiodic acid is used in place of hydrochloric acid, the corresponding bromo- or iodoformamidinium salts are obtained.

The synthesis takes place by metering nitrolime into from 1 to 6, preferably 2 to 4, equivalents of acid. It is also possible, in particular, to use mixtures of mineral acids, e.g. hydrochloric acid/sulfuric acid or hydrochloric acid/ phosphoric acid in a ratio of from 20/1 to 5/1, in particular 15/1 to 8/1. These mixtures have the advantage that heavy metals present in the reaction mixture are simultaneously precipitated.

It may also be advantageous to employ complexing agents such as aminopolycarboxylates, for example EDTA, or aminopolyphosphonates, and oxidizing agents, for example $H_2O_2$, to remove odoriferous byproducts. The purity of the product is improved in this way without losses of yield occurring.

The purity of the haloformamidinium salt formed can also be increased by carrying out the reaction under reduced pressure, preferably under from 100 to 900 mbar, in order to remove volatile byproducts, especially volatile sulfur compounds.

The nitrolime is normally added in equal portions over a period of from 0.5 to 10 h, in particular from 2 to 5 h, so that the required reaction temperature can be maintained by cooling. Usual reaction temperatures are in the range from −10 to 100° C., in particular from 0 to 40° C.

After the reaction is complete, the haloformamidinium salt which has formed can be reacted directly, after removal of resulting inorganic byproducts such as $CaSO_4$, $CaCl_2$, $CaPO_4$ and carbon, without further purification steps with primary or secondary amines of the formula III to give the corresponding guanidinium salts.

The further reaction of the haloformamidinium salt with primary or secondary amines can be carried out in water or a water-miscible solvent or a mixture thereof. The reaction is, as a rule, carried out at a pH in the region of the pK of the amine, i.e. at a pH of from 6 to 14, preferably 8 to 12.

The pH can be maintained by using, inter alia, bases such as NaOH, KOH, LiOH, $Ca(OH)_2$, $Ba(OH)_2$, $Mg(OH)_2$ or $Na_2CO_3$.

The reaction temperatures are in the range from 0 to 100° C., preferably from 10 to 80° C., particularly preferably from 20 to 70° C.

The reactants can be added in any sequence. A preferred embodiment is one in which the haloformamidinium salt, in particular chloroformamidinium chloride, is added dropwise to a solution of the primary or secondary amine.

The addition may extend over a period of from 0.5 to 10 h, preferably 0.5 to 6 h, particularly preferably 1 to 3 h. After the addition, stirring is usually continued for from 0.5 to 10 h, preferably 1 to 3 h.

Any precipitated inorganic byproducts are removed at from 20 to 100° C., in particular from 50 to 90° C.

The molar ratio of haloformamidinium salts to primary or secondary amines in the range from 0.9 to 5.0, preferably 1.0 to 2.0.

Particularly high conversions can be achieved by, for example, employing the low-cost, technical chloroformamidinium chloride in excess relative to the amine, which is frequently uneconomic in the case of pure cyanamide or pure chloroformamidinium chloride.

A particular advantage of the process is that the yields of guanidinium salts are higher on use of crude haloformamidinium salt, because of the omission of purification steps, than on preparation and further reaction of pure haloformamidinium salts. In addition, the novel process is industrially simpler because of the smaller number of steps.

The purity of the guanidinium salt isolated in the novel process is comparable with that of material prepared from pure starting materials. This is particularly attributable to the high purity of the technical haloformamidinium salt.

The substituted guanidinium compounds which are formed can, as a rule, be isolated in a manner known per se. In the case of final products which are formed as crystals in the reaction, the isolation can take place by simple filtration, washing and, where appropriate, recrystallization. If the final products do not result as crystals, they can be isolated, for example, by extraction with organic solvents at strongly basic pH, followed by crystallization or, where appropriate, distillation.

The process for preparing substituted guanidinium derivatives is explained in detail in the following examples.

EXAMPLE 1

Preparation of Creatine

Stage 1: Preparation of Chloroformamidinium Chloride from Nitrolime 50 g of nitrolime with a $CaCN_2$ content of 43% by weight were added over the course of 2 h, while cooling in ice, to a mixture of 300 g of 20% by weight aqueous hydrochloric acid and 1 g of 85% by weight phosphoric acid. The temperature was kept at from 5 to 10° C. During the addition of nitrolime, 50 l/h air was passed through the mixture. Following the nitrolime addition, the suspension was stirred at 5 to 10° C. for 5 h and filtered. The residue on the filter was washed with a total of 150 ml of water. The combined water washings and mother liquor showed a content of 26.8 g of chloroformamidinium chloride (by HPLC), corresponding to a yield of 89%.

Stage 2:

The aqueous solution obtained in Stage 1 was added dropwise over the course of 3 h at 20 to 30° C. to a mixture of 55.4 g of a 40% by weight aqueous sodium sarcosinate solution and 16 g of 50% strength sulfuric acid. The pH of the solution was kept at 10 by means of 50% strength NaOH. After the addition, the mixture was stirred at room temperature for 5 h and then filtered at 60° C., and the filtrate was concentrated to about 50 to 60% of the total weight under reduced pressure at max. 60° C. The precipitate which separated out after cooling was filtered off, washed with 3×20 ml of cold water and dried. 22.6 g of creatine monohydrate with a purity >99% were obtained.

We claim:

1. A process for preparing substituted guanidine compounds of the formula I,

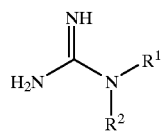

I which comprises reacting haloformamidinium salts of the formula II,

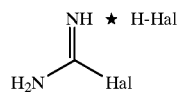

II where Hal can be Cl, F, Br and I, with primary or secondary amines of the formula III

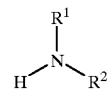

III where the substituents $R^1$ and $R^2$ have the following meanings independently of one another:

$R^1$ H, $C_1$–$C_{20}$-alkyl, $C_2$–$C_{10}$-alkenyl, $C_3$–$C_8$-cycloalkyl;

$R^2$ $C_1$–$C_{20}$-alkyl, $C_2$–$C_{10}$-alkenyl, $C_3$–$C_8$-cycloalkyl, —($C_1$–$C_{20}$-alkylene)—$COOR^3$, —($C_1$–$C_{20}$-alkylene)—$CONR^4R^5$, —($C_1$–$C_{20}$-alkylene)—CN, —($C_1$–$C_{20}$-alkylene)—$SO_2R^6$, —[$(CH_2)_m$—X—]$_p$—[$(CH_2)_n$—Y—]$_q$—[$(CH_2)_o$]$_r$—Z;

m, n, o
    0 to 10;

p, q, r
    0 to 50,000;

X O, NH;

Y N—[$(CH_2)_m$—X—]$_p$—[$(CH_2)_n$—Y—]$_q$—[$(CH_2)_o$]$_r$—Z;

Z OH, $NH_2$;

$R^3$ H, $C_1$–$C_{20}$-alkyl, $C_2$–$C_{10}$-alkenyl, $C_3$–$C_8$-cycloalkyl, $C_6$–$C_{18}$-aryl, Na, K, Li, Ca, Mg, $N(R^7)_4$;

$R^4$ and $R^5$ independently of one another
    H, $C_1$–$C_{20}$-alkyl, $C_2$–$C_{10}$-alkenyl, $C_3$–$C_8$-cycloalkyl, $C_6$–$C_{18}$-aryl;

$R^6$ $OR^8$, $N(R^9)_2$;

$R^7$ H, $C_1$–$C_{20}$-alkyl;

$R^8$ H, $C_1$–$C_{20}$-alkyl, $C_2$–$C_{10}$-alkenyl, $C_3$–$C_8$-cycloalkyl, $C_6$–$C_{18}$-aryl, Na, K, Li, Ca, Mg, $N(R^7)_4$;

$R^9$ H, $C_1$–$C_{20}$-alkyl, $C_2$–$C_{10}$-alkenyl, $C_3$–$C_8$-cycloalkyl, $C_6$–$C_{18}$-aryl.

2. A process for preparing substituted guanidine compounds as claimed in claim 1, wherein the haloformamidinium salt of the formula II prepared from nitrolime is reacted directly, without isolation, with amines of the formula III.

3. A process for preparing substituted guanidine compounds as claimed in claim 1, wherein the amines of the formula III are reacted with chloroformamidinium chloride.

4. A process for preparing substituted guanidine compounds as claimed in claim 1, wherein the amines are compounds selected from the group of amino carboxylic acids, their esters, amides and nitriles, and amino sulfonic acids and their esters and amides.

5. A process for preparing substituted guanidine compounds as claimed in claim 1, wherein the amines are compounds selected from the group of alkylene diamines, dialkylene triamines, trialkylene tetramines and polyalkylenepolyamines.

* * * * *